(12) United States Patent
Morris, Jr.

(10) Patent No.: US 9,714,650 B2
(45) Date of Patent: Jul. 25, 2017

(54) PUMPING SYSTEM

(71) Applicant: Matthew G. Morris, Jr., San Diego, CA (US)

(72) Inventor: Matthew G. Morris, Jr., San Diego, CA (US)

(*) Notice: Subject to any disclaimer, the term of this patent is extended or adjusted under 35 U.S.C. 154(b) by 595 days.

(21) Appl. No.: 14/105,622

(22) Filed: Dec. 13, 2013

(65) Prior Publication Data

US 2014/0363313 A1 Dec. 11, 2014

Related U.S. Application Data

(60) Provisional application No. 61/833,831, filed on Jun. 11, 2013.

(51) Int. Cl.
*F04B 43/02* (2006.01)
*F04B 43/00* (2006.01)
*A61M 5/142* (2006.01)

(52) U.S. Cl.
CPC ....... *F04B 43/026* (2013.01); *A61M 5/14224* (2013.01); *A61M 5/14228* (2013.01); *F04B 43/0054* (2013.01); *A61M 2205/12* (2013.01); *A61M 2205/128* (2013.01); *F04B 43/025* (2013.01); *F04B 43/028* (2013.01)

(58) Field of Classification Search
CPC .. F04B 43/026; F04B 43/0054; F04B 43/025; F04B 43/028; A61M 5/14224; A61M 5/142282; A61M 2205/128; A61M 2205/121
USPC .............................................. 417/479, 413.1
See application file for complete search history.

(56) References Cited

U.S. PATENT DOCUMENTS

| | | | |
|---|---|---|---|
| 3,597,114 | A | 8/1971 | Hrdina |
| 3,976,402 | A | 8/1976 | Lundquist |
| 3,985,133 | A | 10/1976 | Jenkins et al. |
| 4,065,230 | A | 12/1977 | Gezari |
| 4,126,132 | A | 11/1978 | Portner et al. |
| 4,140,118 | A | 2/1979 | Jassawalla |
| 4,142,524 | A | 3/1979 | Jassawalla et al. |
| 4,165,208 | A | 8/1979 | Lundquist |
| 4,178,927 | A | 12/1979 | Lundquist |
| 4,199,307 | A | 4/1980 | Jassawalla |
| 4,236,880 | A | 12/1980 | Archibald |
| 4,265,600 | A | 5/1981 | Mandroian |
| 4,265,601 | A | 5/1981 | Mandroian |
| 4,273,121 | A | 6/1981 | Jassawalla |
| 4,276,004 | A | 6/1981 | Hahn |
| 4,290,346 | A | 9/1981 | Bujan |
| 4,322,201 | A | 3/1982 | Archibald |
| 4,342,312 | A | 8/1982 | Whitney et al. |
| 4,382,753 | A | 5/1983 | Archibald |
| 4,410,322 | A | 10/1983 | Archibald |

(Continued)

*Primary Examiner* — Dominick L Plakkoottam
*Assistant Examiner* — Connor Tremarche
(74) *Attorney, Agent, or Firm* — Sughrue Mion, PLLC

(57) ABSTRACT

Provided is a pumping system that includes a parallel dual chamber pumping mechanism and an attachable disposable cassette. The disposable cassette includes a multi-laminate membrane which facilitates efficient, accurate and uniform delivery of fluids. The multi-laminate membrane is held in intimate contact with the pumping fingers of the pumping mechanism by electrostatic or magnetic attraction, thereby allowing the pump to pull a vacuum without the need for a preloaded elastomeric pumping segment.

21 Claims, 7 Drawing Sheets

(56) References Cited

U.S. PATENT DOCUMENTS

| | | | |
|---|---|---|---|
| 4,450,079 | A | 5/1984 | Farr |
| 4,456,009 | A | 6/1984 | Vcelka et al. |
| 4,468,222 | A | 8/1984 | Lundquist |
| 4,519,792 | A | 5/1985 | Dawe |
| 4,557,725 | A | 12/1985 | Heyne et al. |
| 4,594,058 | A | 6/1986 | Fischell |
| 4,601,702 | A | 7/1986 | Hudson |
| 4,657,490 | A | 4/1987 | Abbott |
| 4,768,547 | A | 9/1988 | Danby et al. |
| 4,784,577 | A | 11/1988 | Ritson et al. |
| 4,798,589 | A | 1/1989 | Tseo |
| 4,808,089 | A | 2/1989 | Buchholtz et al. |
| 4,818,186 | A | 4/1989 | Pastrone et al. |
| 4,828,464 | A | 5/1989 | Maier et al. |
| 4,838,856 | A | 6/1989 | Mulreany et al. |
| 4,838,860 | A | 6/1989 | Groshong et al. |
| 4,840,542 | A | 6/1989 | Abbott |
| 4,842,584 | A | 6/1989 | Pastrone |
| 4,845,487 | A | 7/1989 | Frantz et al. |
| 4,846,636 | A | 7/1989 | Danby et al. |
| 4,850,807 | A | 7/1989 | Frantz |
| 4,850,817 | A | 7/1989 | Nason et al. |
| 4,850,980 | A | 7/1989 | Lentz et al. |
| 4,857,048 | A | 8/1989 | Simons et al. |
| 4,872,813 | A | 10/1989 | Gorton et al. |
| 4,898,579 | A | 2/1990 | Groshong et al. |
| 4,995,864 | A | 2/1991 | Bartholomew et al. |
| 5,006,050 | A | 4/1991 | Cooke et al. |
| 5,055,001 | A * | 10/1991 | Natwick ............... F04B 43/082 417/479 |
| 5,098,262 | A | 3/1992 | Wecker et al. |
| 5,114,314 | A | 5/1992 | Fujimoto |
| 5,302,093 | A | 4/1994 | Owens et al. |
| 5,332,372 | A | 7/1994 | Reynolds |
| 5,378,126 | A | 1/1995 | Abrahamson et al. |
| 5,462,256 | A | 10/1995 | Minick et al. |
| 5,464,392 | A | 11/1995 | Epstein et al. |
| 5,526,962 | A | 6/1996 | Huggenberger |
| 5,551,850 | A | 9/1996 | Williamson et al. |
| 5,554,013 | A | 9/1996 | Owens et al. |
| 5,577,891 | A * | 11/1996 | Loughnane ........... F04B 43/082 417/412 |
| 5,586,868 | A | 12/1996 | Lawless et al. |
| 5,609,572 | A | 3/1997 | Lang |
| 5,630,706 | A | 5/1997 | Yang |
| 5,718,569 | A * | 2/1998 | Holst ..................... F04B 43/02 137/624.18 |
| 5,755,561 | A | 5/1998 | Couillard et al. |
| 5,888,056 | A | 3/1999 | Kim |
| 5,916,197 | A | 6/1999 | Reilly et al. |
| 5,921,951 | A | 7/1999 | Morris |
| 5,935,099 | A * | 8/1999 | Peterson ............... A61M 5/172 604/65 |
| 5,989,423 | A | 11/1999 | Kamen et al. |
| 6,110,410 | A * | 8/2000 | Owens ............... A61M 5/14224 156/274.4 |
| 6,152,702 | A | 11/2000 | Codina et al. |
| 6,179,586 | B1 | 1/2001 | Herb et al. |
| 6,197,000 | B1 | 3/2001 | Reilly et al. |
| 6,210,361 | B1 | 4/2001 | Kamen et al. |
| 6,227,818 | B1 | 5/2001 | Falk et al. |
| 6,264,439 | B1 | 7/2001 | Falk et al. |
| 6,280,406 | B1 * | 8/2001 | Dolecek ............... A61M 1/3624 210/645 |
| 6,283,943 | B1 | 9/2001 | Dy et al. |
| 6,293,756 | B1 | 9/2001 | Andersson |
| 6,355,024 | B1 | 3/2002 | Small et al. |
| 6,413,239 | B1 | 7/2002 | Burns et al. |
| 6,454,548 | B2 | 9/2002 | Falk et al. |
| 6,464,667 | B1 | 10/2002 | Kamen et al. |
| 6,468,261 | B1 | 10/2002 | Small et al. |
| 6,471,436 | B1 | 10/2002 | Gjata et al. |
| 6,537,249 | B2 | 3/2003 | Kriesell et al. |
| 6,623,455 | B2 | 9/2003 | Small et al. |
| 6,669,669 | B2 | 12/2003 | Flaherty et al. |
| 6,682,500 | B2 | 1/2004 | Soltanpour et al. |
| 6,702,779 | B2 | 3/2004 | Connelly et al. |
| 6,749,587 | B2 | 6/2004 | Flaherty |
| 6,796,777 | B2 | 9/2004 | Falk et al. |
| 6,805,693 | B2 | 10/2004 | Gray et al. |
| 6,877,713 | B1 | 4/2005 | Gray et al. |
| 6,948,918 | B2 | 9/2005 | Hansen |
| 6,997,921 | B2 | 2/2006 | Gray et al. |
| 7,064,472 | B2 | 6/2006 | Pelrine et al. |
| 7,104,767 | B2 | 9/2006 | Lee |
| 7,232,423 | B2 | 6/2007 | Mernoe |
| 7,232,430 | B2 | 6/2007 | Carlisle et al. |
| 7,278,985 | B2 | 10/2007 | Agerup |
| 7,360,999 | B2 | 4/2008 | Nelson et al. |
| 7,362,032 | B2 | 4/2008 | Pelrine et al. |
| 7,394,182 | B2 | 7/2008 | Pelrine et al. |
| 7,396,353 | B2 | 7/2008 | Lorenzen et al. |
| 7,402,154 | B2 | 7/2008 | Holst et al. |
| 7,614,857 | B2 | 11/2009 | Fuechslin et al. |
| 7,762,793 | B2 | 7/2010 | Gray et al. |
| 7,776,029 | B2 | 8/2010 | Whitehurst et al. |
| 7,785,293 | B2 | 8/2010 | Gray et al. |
| 7,854,718 | B2 * | 12/2010 | Gura ................... A61M 1/1696 210/645 |
| 7,867,193 | B2 | 1/2011 | McKenna et al. |
| 7,867,194 | B2 | 1/2011 | Fiering et al. |
| 7,905,710 | B2 | 3/2011 | Wang et al. |
| 7,911,115 | B2 | 3/2011 | Pelrine et al. |
| 7,922,695 | B2 | 4/2011 | Wiegel et al. |
| 7,951,112 | B2 | 5/2011 | Patzer |
| 8,052,642 | B2 | 11/2011 | Harr et al. |
| 8,053,721 | B2 | 11/2011 | Bisch et al. |
| 8,075,527 | B2 | 12/2011 | Rush et al. |
| 8,075,546 | B2 | 12/2011 | Carlisle et al. |
| 8,079,983 | B2 | 12/2011 | Rush et al. |
| 8,079,984 | B2 | 12/2011 | Rush et al. |
| 8,079,999 | B2 | 12/2011 | Duchon et al. |
| 8,083,718 | B2 | 12/2011 | Rush et al. |
| 8,088,106 | B2 | 1/2012 | Siefert |
| 8,133,205 | B2 | 3/2012 | Rhinehart et al. |
| 8,137,314 | B2 | 3/2012 | Mounce et al. |
| 8,142,397 | B2 | 3/2012 | Patzer |
| 8,147,448 | B2 | 4/2012 | Sundar et al. |
| 8,162,874 | B2 | 4/2012 | Whitehead et al. |
| 8,162,903 | B2 | 4/2012 | Reilly et al. |
| 8,172,799 | B2 | 5/2012 | Mohiuddin et al. |
| 8,172,800 | B2 | 5/2012 | Rush et al. |
| 8,202,250 | B2 | 6/2012 | Stutz, Jr. |
| 8,202,267 | B2 | 6/2012 | Field et al. |
| 8,282,366 | B2 | 10/2012 | Hilber et al. |
| 8,328,537 | B2 | 12/2012 | Rochat |
| 8,333,568 | B2 | 12/2012 | Luongo et al. |
| 8,337,488 | B2 | 12/2012 | Imran |
| 8,377,004 | B2 | 2/2013 | Wiegel et al. |
| 8,398,595 | B2 | 3/2013 | Lee |
| 8,414,522 | B2 | 4/2013 | Kamen et al. |
| 8,414,535 | B2 | 4/2013 | Jacobsen et al. |
| 8,444,597 | B2 | 5/2013 | Sullivan et al. |
| 8,465,454 | B2 | 6/2013 | Kirkpatrick |
| 8,475,409 | B2 | 7/2013 | Tsoukalis |
| 8,486,018 | B2 | 7/2013 | Kamen et al. |
| 8,496,646 | B2 | 7/2013 | Kamen et al. |
| 8,523,839 | B2 | 9/2013 | Siefert |
| 8,551,037 | B2 | 10/2013 | Suchecki et al. |
| 8,551,055 | B2 | 10/2013 | McConnell et al. |
| 8,579,884 | B2 | 11/2013 | Lanier, Jr. et al. |
| 8,596,997 | B2 | 12/2013 | Grip |
| 8,597,244 | B2 | 12/2013 | Mernoe |
| 8,608,700 | B2 | 12/2013 | Rubel |
| 2005/0209563 | A1 * | 9/2005 | Hopping ................. A61M 1/28 604/151 |
| 2007/0278155 | A1 * | 12/2007 | Lo .......................... A61M 1/16 210/646 |
| 2012/0022494 | A1 * | 1/2012 | Kirkpatrick ....... A61M 5/16877 604/500 |

* cited by examiner

PUMPING SYSTEM

CROSS REFERENCE TO RELATED APPLICATION(S)

This application claims the benefit of priority under 35 U.S.C. §119(e) of U.S. Ser. No. 61/833,831, filed Jun. 11, 2013, the entire content of which is incorporated herein by reference.

BACKGROUND OF THE INVENTION

Field of the Invention

The invention relates generally to fluid pumping technology and more specifically to a cassette pump having a multi-laminate membrane with magnetic and/or conductive properties that attaches to pumping fingers through electrostatic or magnetic forces.

Background Information

Cassette pumps provide a convenient and relatively low cost device for infusing drugs into the body of a patient. These pumps employ cassettes made of injection molded plastic, which are discarded after use with a patient. A pump designed to operate with a particular configuration of cassette includes a drive mechanism that actuates the cassette to deliver fluids to a patient. Such pumps are typically controlled by a microprocessor that can be programmed to deliver a predefined volume of medicinal fluid, at a predefined rate, and over a predefined time. Cassette pumps are typically more accurate than peristaltic pumps and are able to deliver drugs at a relatively wide range of rates and volumes.

There have been no significant breakthroughs in large volume perenteral (LVP) pumping mechanisms since the first cassette and peristaltic pumping systems were introduced over 30 years ago. Large volume infusion pumps on the market today are products of an evolutionary process of iterative design, evolving from the vented glass bottle and roller clamp controlled drip rate through electronic drip counters, controllers and finally volume displacement pumps. Thus, advances in the industry have been incremental system refinements at best, having more to do with improvements in motor control software that leverage advancements in sensor technology to compensate irregular mechanical pumping performance with complex software motor drive algorithms. Software control has driven steady improvements in instrument accuracy and flow uniformity over the years; however since the fundamental pumping mechanisms have not changed, inherent weaknesses remain. The difficulties that these pumping systems have always had in accommodating high fluid viscosities, wide ranges of infusion rates, variations in differential pressure, and a variety of other use conditions, have not been addressed.

Performance related issues fall into four general categories; system compliance, component tolerance sensitivity, dimensional stability of the disposable/instrument interface and the serial nature of the peristaltic and single chamber pumping systems. Errors induced by electronic hardware tolerances and software control are relatively small and are outside the scope of this invention. Thus, the invention relates to Large Volume Perenteral (LVP) infusion devices and addresses inherent issues with current traditional systems which influence the overall performance of fluid delivery.

SUMMARY OF THE INVENTION

The present invention relates to a parallel dual chamber pumping mechanism and an attachable disposable membrane which facilitates efficient, accurate and uniform delivery of fluids, and provides an effective interface for sensing pressure. The multi-laminate membrane is held in intimate contact with the pumping fingers, thereby allowing the pump to pull a vacuum without the need for a preloaded, high spring rate, elastomeric pumping segment.

Accordingly, in one aspect, the invention provides a pumping system. The pumping system includes a disposable cassette and a pumping mechanism. The disposable cassette includes a body having a sealed top side, an open bottom side, an inlet port disposed on a first end and an outlet port disposed on a second end, a first pumping chamber disposed within the open bottom side between a first inlet valve and a first outlet valve, a second pumping chamber disposed within the open bottom side between a second inlet valve and a second outlet valve, wherein the first and second pumping chambers are positioned in parallel with each other, and an electrostatic membrane adhered to and sealing the open bottom side defining a fluid path between the inlet port and the outlet port. The pumping mechanism includes a chassis configured for removable attachment to the disposable cassette, a motor disposed within a length of the chassis and positioned in parallel to the flow path, a camshaft disposed adjacent to and in mechanical communication with the motor, wherein the camshaft comprises a plurality of lobes disposed along a length thereof, a first finger drive arm hingedly attached to the chassis and positioned parallel to the motor, wherein a bottom portion of the first finger drive arm is in mechanical communication with the camshaft, a second finger drive arm hingedly attached to the chassis and positioned opposing the first finger drive arm, wherein a bottom portion of the second finger drive arm is in mechanical communication with the camshaft, and wherein the first and second finger drive arms are 180° out of phase with each other, a first pumping finger face plate fixedly attached to a top portion of the first finger drive arm, and a second pumping finger face plate fixedly attached to a top portion of the second finger drive arm, wherein the first and second pumping finger face plates are configured for electrostatic attachment to the electrostatic membrane, and a plurality of valve arms hingedly attached to the chassis, wherein a lower portion of each valve arm is in mechanical communication with one of the plurality of lobes on the camshaft and an upper portion of each valve arm is configured to respectively actuate each of the first and second inlet valves and the first and second outlet valves.

In various embodiments, the camshaft includes an inlet valve lobe and an outlet valve lobe, each disposed at opposite ends of the camshaft and 180° out of phase from each other. The plurality of valve arms may include a first and second inlet valve arm, and a first and second outlet valve arm, wherein the first inlet valve and second outlet valve arms are configured to actuate the respective valves simultaneously, and wherein the second inlet valve and first outlet valve arms are configured to actuate the respective valves simultaneously.

The plurality of lobes may include a main lobe configured to actuate each of the first and second finger drive arms, a first valve lobe, and a second valve lobe, wherein the first valve lobe is configured to actuate the valve arms corresponding to the first and second inlet valves, and the second valve lobe is configured to actuate the valve arms corresponding to the first and second outlet valves.

In various embodiments, the electrostatic membrane is a thin film multi-laminate membrane. The thin film multi-laminate membrane may include a first layer configured to adhere to the open bottom side of the body, a second layer configured to hold a static charge, and a third layer configured to resist abrasion, wherein the first, second, and third layers are laminated as a single membrane.

The pumping system may also include a plurality of strain gauges disposed on the pumping mechanism and configured to monitor fluid pressure within the first and second pumping chambers. The plurality of strain gauges may include a first and a second strain gauge, each disposed on one of the first and second finger drive arms. In certain embodiments, the plurality of strain gauges may include a first and a second strain gauge, each disposed on a surface of one of the first and second pumping finger face plates. The first and second strain gauges may be disposed on the surface opposite to the electrostatic attachment to the electrostatic membrane.

The inlet port of the disposable cassette may be configured for fluid communication with a fluid reservoir and the outlet port may be configured for attachment to downstream supply tubing for intravenous administration of the fluid to a subject.

In another aspect, the invention provides a pumping system. The pumping system includes a disposable cassette and a pumping mechanism. The disposable cassette includes a body having a sealed top side, an open bottom side, an inlet port disposed on a first end and an outlet port disposed on a second end, a first pumping chamber disposed within the open bottom side between a first inlet valve and a first outlet valve, a second pumping chamber disposed within the open bottom side between a second inlet valve and a second outlet valve, wherein the first and second pumping chambers are positioned in parallel with each other, and a multi-laminate membrane adhered to and sealing the open bottom side defining a fluid path between the inlet port and the outlet port. The pumping mechanism includes a chassis configured for removable attachment to the disposable cassette, a motor disposed within a length of the chassis and positioned in parallel to the flow path, a camshaft disposed adjacent to and in mechanical communication with the motor, wherein the camshaft comprises a plurality of lobes disposed along a length thereof, a first finger drive arm hingedly attached to the chassis and positioned parallel to the motor, wherein a bottom portion of the first finger drive arm is in mechanical communication with the camshaft, a second finger drive arm hingedly attached to the chassis and positioned opposing the first finger drive arm, wherein a bottom portion of the second finger drive arm is in mechanical communication with the camshaft, and wherein the first and second finger drive arms are 180° out of phase with each other, an array of permanent magnets fixedly attached to a top portion of the first and second finger drive arms, wherein the permanent magnets are configured for magnetic attachment to the multi-laminate membrane, and a plurality of valve arms hingedly attached to the chassis, wherein a lower portion of each valve arm is in mechanical communication with one of the plurality of lobes on the camshaft and an upper portion of each valve arm is configured to respectively actuate each of the first and second inlet valves and the first and second outlet valves.

In various embodiments, the camshaft includes an inlet valve lobe and an outlet valve lobe, each disposed at opposite ends of the camshaft and 180° out of phase from each other. The plurality of valve arms may include a first and second inlet valve arm, and a first and second outlet valve arm, wherein the first inlet valve and second outlet valve arms are configured to actuate the respective valves simultaneously, and wherein the second inlet valve and first outlet valve arms are configured to actuate the respective valves simultaneously.

The plurality of lobes may include a main lobe configured to actuate each of the first and second finger drive arms, a first valve lobe, and a second valve lobe, wherein the first valve lobe is configured to actuate the valve arms corresponding to the first and second inlet valves, and the second valve lobe is configured to actuate the valve arms corresponding to the first and second outlet valves.

In various embodiments, the multi-laminate membrane is a thin film paramagnetic and/or conductive membrane. The thin film multi-laminate membrane may include a first layer configured to adhere to the open bottom side of the body, a second layer configured to be paramagnetic and/or electrically conductive, and a third layer configured to resist abrasion, wherein the first, second, and third layers are laminated as a single membrane.

The pumping system may also include a plurality of strain gauges disposed on the pumping mechanism and configured to monitor fluid pressure within the first and second pumping chambers. The plurality of strain gauges may include a first and a second strain gauge, each disposed on one of the first and second finger drive arms. In certain embodiments, the plurality of strain gauges may include a first and a second strain gauge, each disposed on a surface of one of the first and second pumping fingers. The first and second strain gauges may be disposed on the surface opposite to the magnetically or electrostatically coupled membrane.

The inlet port of the disposable cassette may be configured for fluid communication with a fluid reservoir and the outlet port may be configured for attachment to downstream supply tubing for intravenous administration of the fluid to a subject.

In another aspect, the invention provides a disposable cassette. The disposable cassette includes a body having a sealed top side, an open bottom side, an inlet port disposed on a first end and an outlet port disposed on a second end, a first pumping chamber disposed within the open bottom side between a first inlet valve and a first outlet valve, a second pumping chamber disposed within the open bottom side between a second inlet valve and a second outlet valve, wherein the first and second pumping chambers are positioned in parallel with each other, and a multi-laminate membrane adhered to and sealing the open bottom side defining a fluid path between the inlet port and the outlet port.

In yet another aspect, the invention provides a pumping mechanism. The pumping mechanism includes a chassis configured for removable attachment to the disposable cassette, a motor disposed within a length of the chassis and positioned in parallel to the flow path, a camshaft disposed adjacent to and in mechanical communication with the motor, wherein the camshaft comprises a plurality of lobes disposed along a length thereof, a first finger drive arm hingedly attached to the chassis and positioned parallel to the motor, wherein a bottom portion of the first finger drive arm is in mechanical communication with the camshaft, a second finger drive arm hingedly attached to the chassis and positioned opposing the first finger drive arm, wherein a bottom portion of the second finger drive arm is in mechanical communication with the camshaft, and wherein the first and second finger drive arms are 180° out of phase with each other, a first pumping finger face plate fixedly attached to a top portion of the first finger drive arm, and a second pumping finger face plate fixedly attached to a top portion of the second finger drive arm, wherein the first and second pumping finger face plates are configured for electrostatic attachment to the electrostatic membrane, and a plurality of valve arms hingedly attached to the chassis, wherein a lower portion of each valve arm is in mechanical communication with one of the plurality of lobes on the camshaft and an upper portion of each valve arm is configured to respectively actuate each of the first and second inlet valves and the first and second outlet valves.

In yet another aspect, the invention provides a pumping mechanism. The pumping mechanism includes a chassis configured for removable attachment to the disposable cassette, a motor disposed within a length of the chassis and positioned in parallel to the flow path, a camshaft disposed adjacent to and in mechanical communication with the motor, wherein the camshaft comprises a plurality of lobes disposed along a length thereof, a first finger drive arm hingedly attached to the chassis and positioned parallel to the motor, wherein a bottom portion of the first finger drive arm is in mechanical communication with the camshaft, a second finger drive arm hingedly attached to the chassis and positioned opposing the first finger drive arm, wherein a bottom portion of the second finger drive arm is in mechanical communication with the camshaft, and wherein the first and second finger drive arms are 180° out of phase with each other, an array of permanent magnets fixedly attached to a top portion of the first and second finger drive arms, wherein the permanent magnets are configured for magnetic attachment to the multi-laminate membrane, and a plurality of valve arms hingedly attached to the chassis, wherein a lower portion of each valve arm is in mechanical communication with one of the plurality of lobes on the camshaft and an upper portion of each valve arm is configured to respectively actuate each of the first and second inlet valves and the first and second outlet valves.

DETAILED DESCRIPTION OF THE INVENTION

Figure 1A:
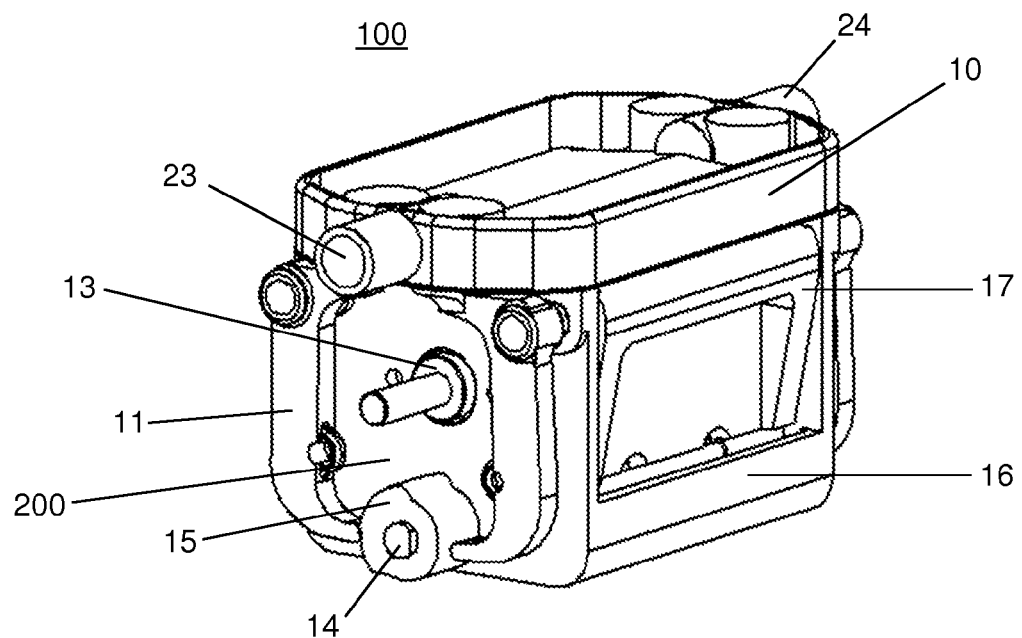
FIGS. 1A-1C are pictorial diagrams showing perspective views of the pumping system, which includes a disposable cassette detachably mounted to a pumping mechanism.
Figure 1B:
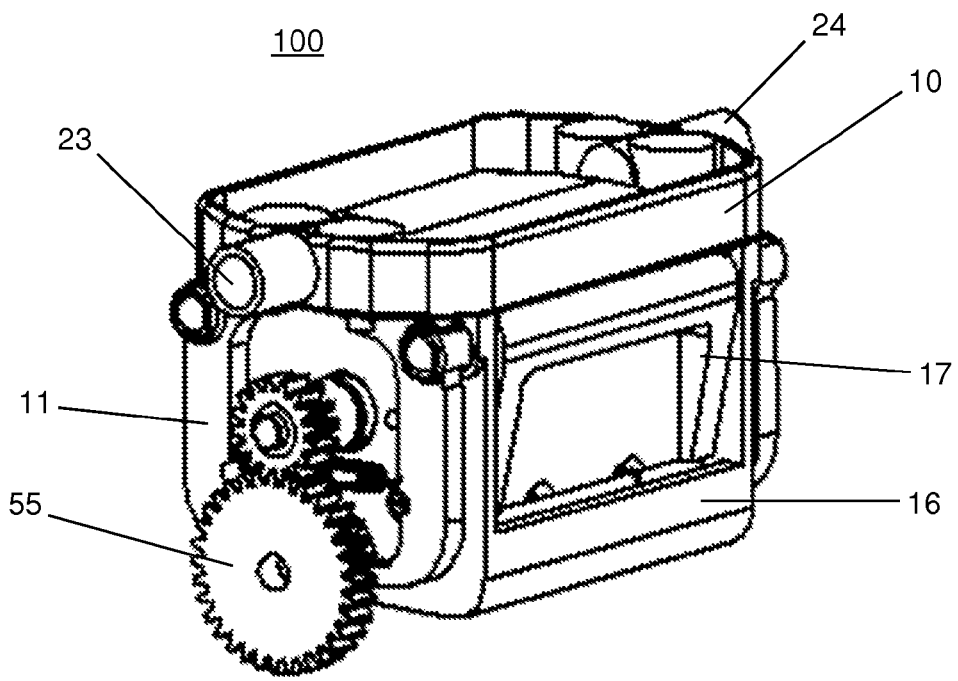
Figure 1C:
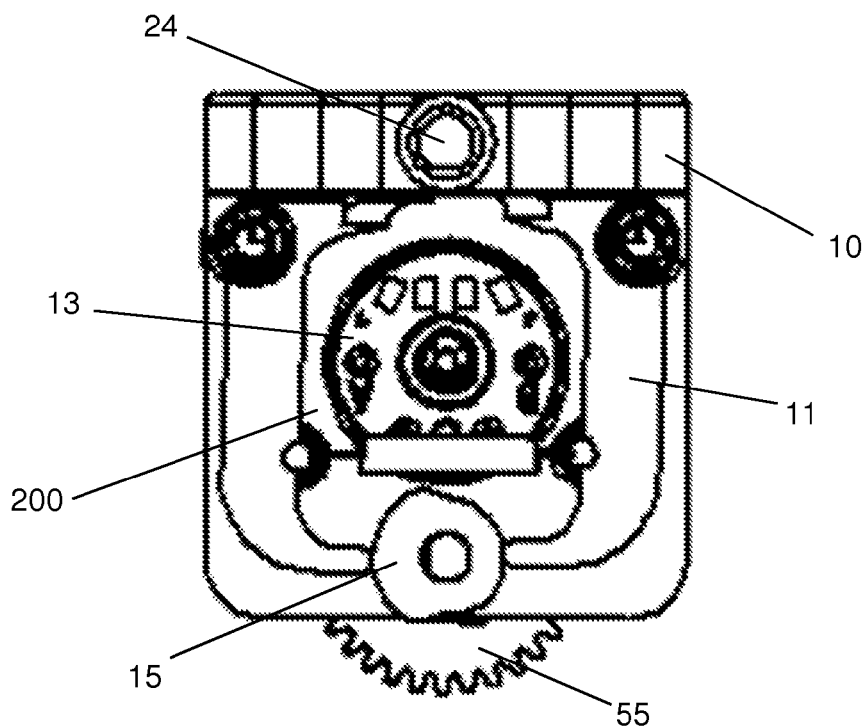
Figure 2A:
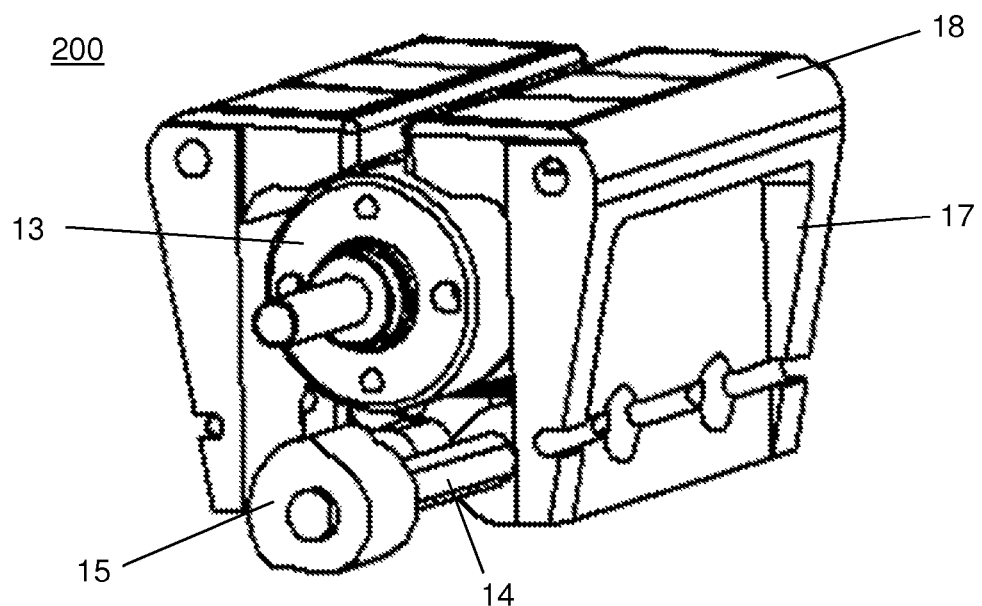
FIGS. 2A and 2B are pictorial diagrams showing perspective views of the pumping mechanism.
Figure 2B:
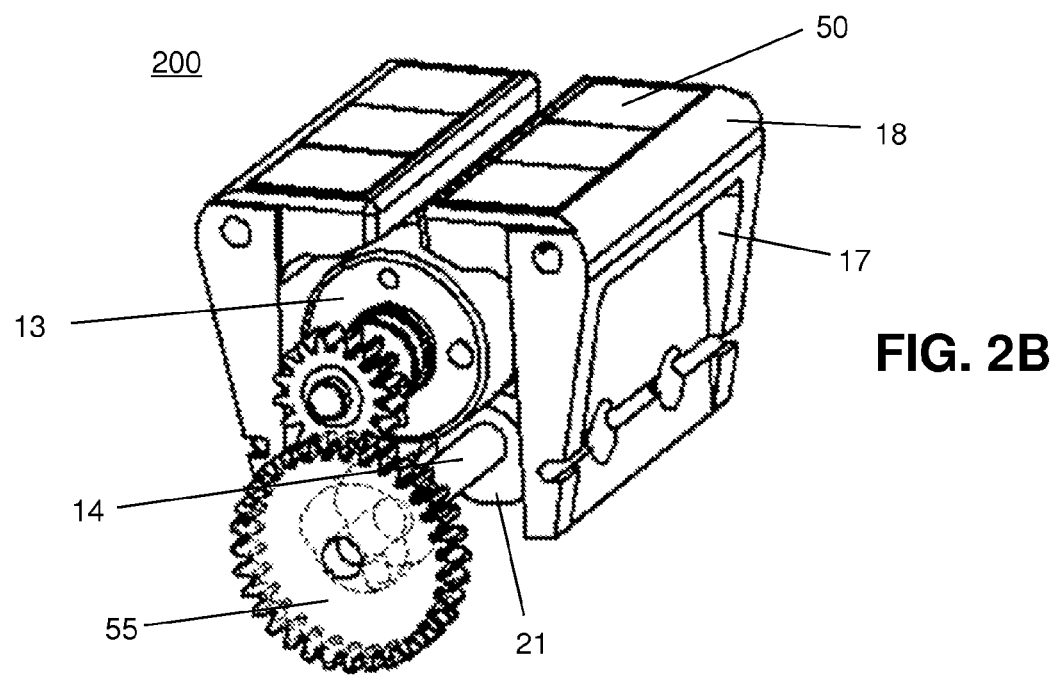

The present invention provides a parallel dual chamber pumping mechanism and an attachable multi-laminate membrane which facilitates efficient, accurate and uniform delivery of fluids, and provides an effective interface for sensing pressure. The multi-laminate membrane is held in intimate contact with the pumping fingers magnetically or electrostatically, thereby allowing the pump to pull a vacuum without the need for a preloaded, high spring rate, elastomeric pumping segment.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As discussed above, conventional cassette pumps employ cassettes made of injection molded plastic, which are discarded after use with a patient. Such cassettes may hereinafter be referred to as "disposables." Such disposables typically rely on displacement of an elastomeric membrane by a pump for movement of a fluid there through. A pump designed to operate with the particular configuration of cassette may hereinafter be referred to as a "pump" or "instrument."

The disposable is manufactured in high volume (millions/year) with a cost of goods sold (COGS) of less than one dollar. The instrument is a relatively low volume (thousands/year) product, with manufacturing costs of thousands of dollars. Both components contribute almost equally (roughly +/−2.5%) to controlling the overall volume rate accuracy of the fluid delivery system (typically +/−5%).

The internal volume of the pumping chamber segment of the disposable controls the volume of fluid displaced each revolution of the pump. Therefore, for a tubular pumping segment as an example, the inside diameter, wall thickness, cut length, material properties and the amount of stretch when assembled all have to be tightly controlled. Many more parts are involved in the instrument side of the tolerance loop. Typical linear peristaltic mechanisms have a basic support frame, front bezel, camshaft, 12 cams, 12 pumping fingers, a reference surface or platen that closes on the disposable to control the compressive load applied to the disposable tubing, numerous springs and a membrane to seal protect sensitive electronic components from fluid ingress.

Volume accuracy is the most commonly referenced performance metric for an infusion device. It is a measure of the difference between the actual fluid delivered over a prescribed time and the desired, or programmed, volume to be delivered. Dimensional tolerances in the instrument and disposable drive the nominal flow rate accuracy for an individual instrument-disposable combination. Another problem is that high stress levels seen by the disposable cause the physical dimensions of the elastomeric tubing or membrane to change over time which affects rate accuracy. To address this problem, tubing pumping segments and membranes have been produced from expensive, high strength, resilient materials.

Volume delivery errors induced by the problems listed above cause accuracy verification testing to be so specific that they do not apply to a wide range of common clinical applications. Thus many manufacturers' rate accuracy claims often have more to do with specifications of the actual product and product marketing, than clinical utility. Published claims are made in the context of laboratory-controlled operating conditions specified by device manufactures and testing agencies. Accuracy claims are based on pump performance at a specific head height, back pressure, instrument orientation and fluid type over the range of delivery rates. Although pumping rate also affects performance, software corrections to motor speeds are typically used to mitigate the influence. An additional constraint typically imposed on volume accuracy testing, is that the disposable tubing sets be exercised or "broken in" before a test is run. Data collection begins only after a designated startup period. As mention above, the high stress levels seen by the elastomer cause the volume delivered by a new/unused disposable to decrease during the first few cycles of operation, as the dimensional and physical properties of the elastomer relax. Steady state operation is attained relatively quickly, however, at low flow rates and for a number of critical intravenous (IV) drugs; this change in volume can be clinically significant.

Nominal volume accuracy is a function of manufacturing tolerances in the instrument, disposable, and instrument-disposable interface. Changes in the rate of fluid delivery over time are caused by the instability of the elastomeric material within the disposable and the overall sensitivity of the pumping mechanism to changes in external operating conditions. Another important consideration is the dimensional control and stability of the disposable-instrument interface. The disposable and instrument should remain parallel and the gap between the disposable and instrument should remain constant in order to ensure rate accuracy.

Conventional LVP devices use volume displacement based pumping systems. The volume delivered during each pumping cycle should be stable and dimensionally well controlled. However, as discussed above, the disposable includes a compliant elastomer manufactured in high volume which is unstable and difficult to inspect and control dimensionally. In addition, it will expand or contract, much like a balloon, with changes in pressure. The volume of fluid displaced during each pumping cycle therefore becomes a function of the differential pressure across the pump. In other words, the greater the pressure upstream feeding the pump, and the larger the tubing cross section, the greater the volume of fluid that is pumped per cycle. The opposite is true if the pump is working against a negative head height or upstream vacuum.

Flow uniformity is a measure of the variations in the rate of fluid delivery, as opposed to volume accuracy which measures only the total volume of fluid delivered over time. Volume accuracy tests can only measure the average delivery rate over the prescribed collection period. The instantaneous delivery rate for a given instrument could deviate significantly, and still maintain the desired total volume of fluid delivered during the duration of an infusion. It is obviously important that critical drug solutions be administered in a well-controlled, steady delivery rate. Large volume infusion devices, due mostly to the serial nature of the fill and delivery stages of their pumping cycles, have performed poorly in this area, relative to syringe based infusion devices. For this reason, syringe pump instruments are preferred for delivering critical, highly concentrated solutions and for neonatal application.

The standard measure for flow uniformity is the trumpet curve. Trumpet curves, or "T" curves, represent the maximum percentage deviation from the programmed infusion rate for prime number time intervals, starting at approximately 2 minutes, the shorter the time interval, the greater the positive and negative deviation from the average rate. As the time interval increases, the positive and negative deviations converge. At approximately 31 minutes, the curves become asymptotic to the nominal infusion rate. The resultant graph looks like the bell of a trumpet. There is work being done to revisit this test, as the body response time to some of the vasoactive drugs is much more rapid than the two minute window measured. In addition, many infusion devices are driven by stepper motors which rotate in discrete increments. Although, this is not an inherent design issue, step resolution should be considered and managed so that the bolus delivered during each motor step and the time interval between steps does not become clinically relevant.

The problem with serial, positive displacement devices is that flow during the pumping cycle is not uniform. As an example, linear peristaltic devices sequentially pinch off the tube, "milking" the solution downstream. After the last finger closes on the tube, the cycle starts over with the first finger. No actual pumping is done during the transition from the last to first finger. This interval of zero flow is mitigated by running the pump as fast as possible through the zero flow phase of the pumping cycle. Pumps that use tandem, chambered cassettes typically address the end of the pumping cycle, or fill time issue by using a dedicated flow compensation chamber downstream from the primary pumping chamber, which continues pumping fluid as the first chamber fills. This system mitigates the necessity to speed up the mechanism at the end of the pumping cycle; however it is optimized for uniform flow at only one downstream, patient side, pressure. There is an inherent issue with this approach. Downstream pressure is trapped in the pumping chambers during each pumping cycle, which increases or decreases the volume of the compliant disposable, depending on whether the differential pressure across the pump is positive or negative. This is much like the upstream pressure effects on peristaltic systems discussed above, however; this trapped volume is released upstream when the instrument upstream valve cycles. Flow rate again becomes a function of the differential pressure across the pump. The degree of influence of the pressure differential depends on the volume and compliance of the disposable and instrument.

Compliance and dimensional instability increase the instrument sensitivity to operating and environmental conditions. Thus, the present invention provides a cost effective and accurate fluid delivery system that is immune to operational and environment extremes. The pumping system described herein solves the above problems by including critical components of the pumping mechanism in the instrument, not the disposable. In addition, the disposable is supported and isolated from pressures generated by the fluids being dispensed/pumped. Additionally, the thicknesses of the disposable tubing and membrane wall do not add to the tolerance stack of components critical to the function and accuracy of the pumping system.

Referring to FIGS. 1-6, the present invention therefore provides a small, lightweight, pumping system 100 that includes a dual chamber pumping mechanism 200 and disposable cassette 10 with an integral thin multi-laminate membrane 32 that facilitates efficient, accurate fluid delivery and an effective method for accurately sensing the pressure of the fluid being pumped without the need for a dedicated feature on the multi-laminate membrane 32 to interface with an independent pressure transducer.

As shown in FIGS. 1A, 1B, 4A-4C, and 5A-5D, the disposable cassette 10 includes a body having a sealed top side, an open bottom side 29, an inlet port 23 disposed on a first end and an outlet port 24 disposed on a second end. The cassette 10 includes two parallel pumping chambers 30 disposed within the open bottom side 29, each respectively positioned between an inlet valve 25 and an outlet valve 28. The inlet port 23 is configured for fluid communication with a fluid reservoir, which contains the fluid to be delivered to a subject. The outlet port 24 is configured for attachment to downstream supply tubing for intravenous administration of the fluid to the subject.

The cross section of the pumping chamber 30 is essentially rectangular, with an inner surface being angled in accordance with a range of motion of pumping fingers of the pumping mechanism. The motion of the pumping fingers 18 is linear so the volume displaced each rotation of the pumping mechanism 200 depends only on the starting and ending positions of the pumping fingers 18.

Figure 5A:
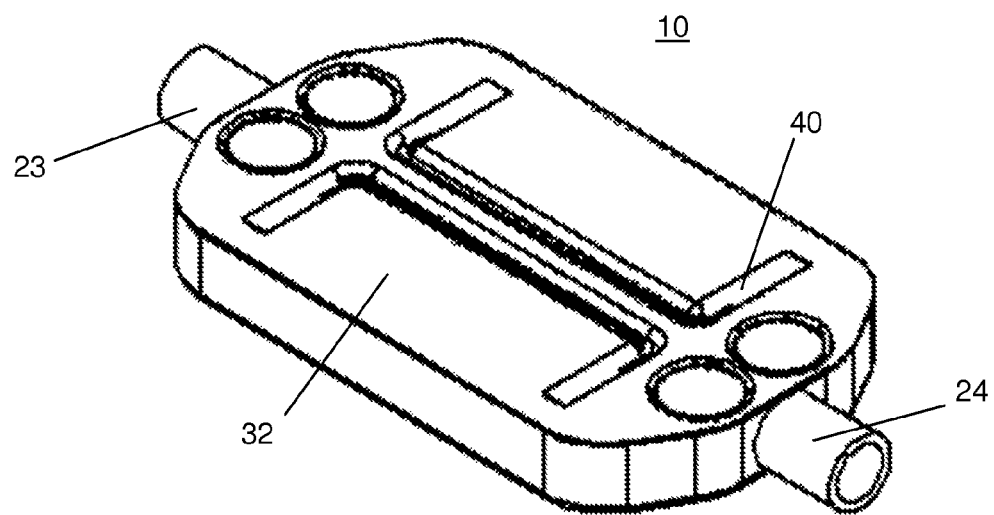
FIGS. 5A-5D are pictorial diagrams showing various views of the disposable cassette including the multi-laminate membrane forming the fluid path.
Figure 5B:
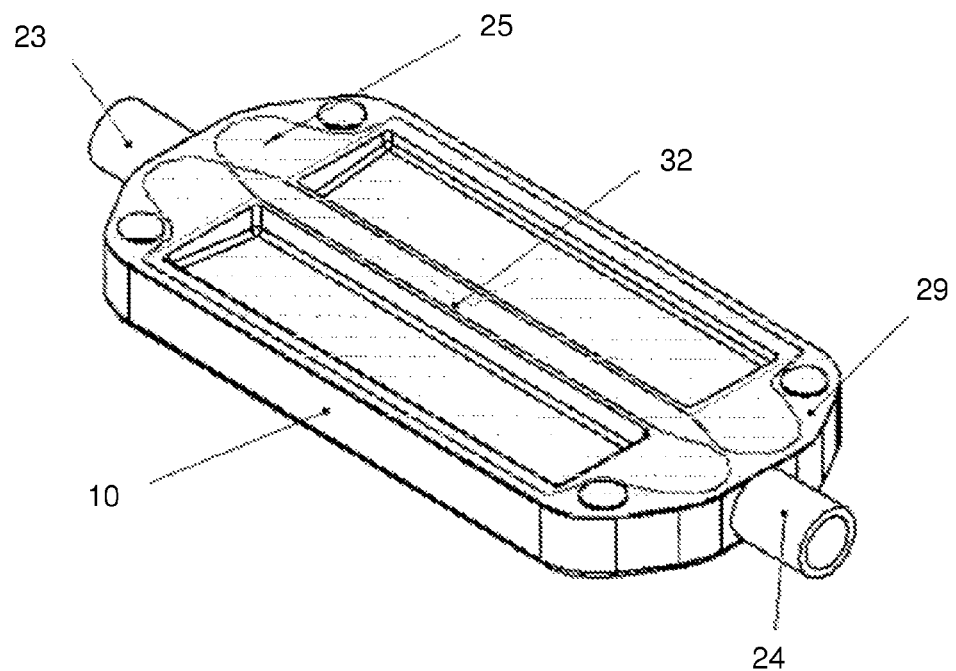
Figure 5C:
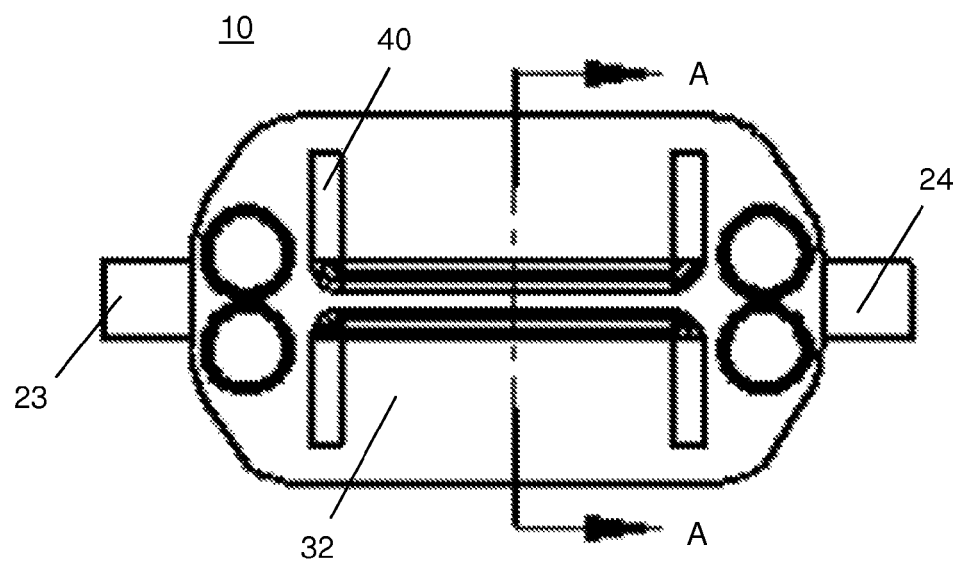

As shown in FIG. 5B, the open bottom side 29 of the cassette 10 is covered by a multi-laminate membrane 32, which defines a fluid path between the inlet 23 and outlet 24 ports of each pumping chamber 30. The multi-laminate membrane may be adhered to the open bottom side 29 of the cassette by any means known in the art. Exemplary means for adhering the multi-laminate membrane 32 to the open bottom side 29 include, but are not limited to, ultrasonic welding, heat-sealing, and solvent-bonding. The thickness of the multi-laminate membrane 32 and resulting volume within the pumping chamber 30 are therefore not part of the tolerance loop, nor are any components in the pumping mechanism (instrument) that establish the initial starting position of the pumping fingers 18. Only the surface area and stroke of the main lobe 21 factor into the total volume displaced during each pumping cycle.

It should be understood that most of the energy expended by traditional infusion pumps is spent compressing the elastomer in the disposable to seal and control the flow of fluid. In various embodiments, the multi-laminate membrane 32 is a thin film membrane that is not stretched by the pumping mechanism 200 and therefore has no effective spring rate. Thus, in various embodiments, the membrane includes a plurality of layers, each overlapping and bonded to the other. In certain embodiments, the plurality of layers includes a first layer configured to adhere to the open bottom side 29 of the disposable cassette 10, a second layer configured to hold a static charge, and a third layer configured to resist abrasion. In other embodiments, the plurality of layers includes a first layer configured to adhere to the open bottom side 29 of the disposable cassette 10, a second layer that is magnetic (e.g., a thin film of steel), and a third layer configured to resist abrasion.

The membrane 32 may be formed by any means known in the art. For example, as discussed above, the membrane 32 may be formed by bonding a plurality of overlapping layers to one another. However, in various embodiments, the membrane 32 may be formed by, for example, over molding or insert molding (where the paramagnetic material is inserted into the mold cavity during the molding process). Alternatively or in addition thereto, a paramagnetic material could be added to a molded or vacuum-formed membrane as a secondary operation (such as bonding), or one or more magnetic inks may be printed onto the finished plastic component to form a membrane having paramagnetic properties.

As discussed above, the membrane is not compressed and sealing the fluid path against uncontrolled free flow of fluid is accomplished by a plurality of valves (25, 28) provided in the disposable. The advantage of coupling the membrane 32 to the pump fingers 18 is elimination of the dependence on dimensional recovery of the membrane (or tube) to provide the negative pressure required to draw fluid into the pumping chamber 30. Thus, the force required by the instrument pumping mechanism 200 to overcome elastomeric disposable preload and the force required to occlude the flow path which generate the working loads on the pumping mechanism 200 is eliminated. It should also be mentioned that subsequent large static loads need to be supported by the mechanism chassis and support structures in the instrument, which would typically increase the size, weight, material strength requirements, and manufacturing costs.

Furthermore, high stresses generated by the pump on the disposable can fatigue an elastomeric material over time, thereby changing the shape and ability of the membrane or tubing material to recover dimensionally. This causes the fluid pumping rate to typically decrease during the course of an infusion. Elastomers are also compliant which causes their shape to change with changes in differential pressure, again changing the pumping rate and accuracy of the instrument.

Figure 5D:
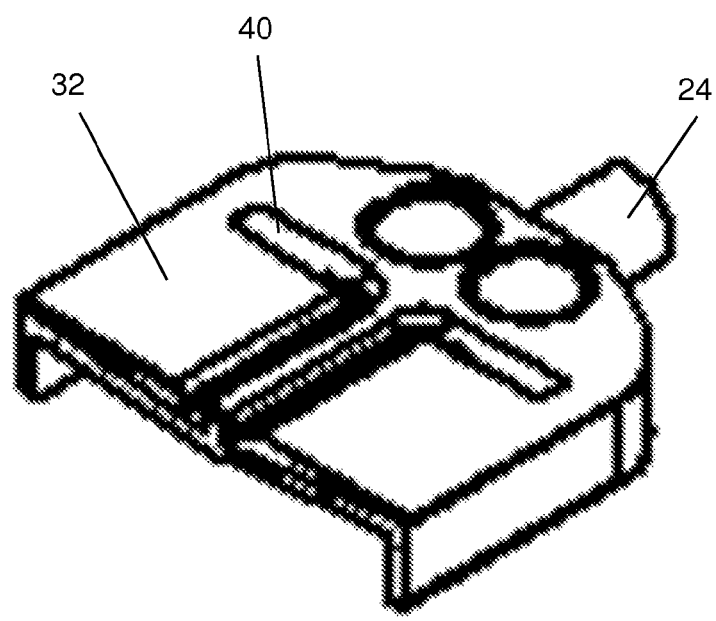

In the present invention, magnetically or electrostatically coupling the membrane 32 to the pumping fingers 18 eliminates the contribution of the membrane 32 to system compliance. The rigidity or dimensional stability of the pumping chamber 30 resides with the instrument 200 which can, more easily and effectively, be managed. In certain embodiments, the membrane 32 is not flat. As shown in FIG. 5A, the membrane 32 may include one or more convolutions 40 configured to allow the membrane 32 to follow the motion of the pumping finger with little or no resistance due to the membrane's relatively high durometer. FIG. 5D is a cross-sectional view of the pumping chamber taken along the section line B-B of FIG. 5C. In addition, because the pumping fingers 18 do not bottom out within the pumping chambers 30, the volume of fluid pumped each cycle is a function only of eccentricity of the camshaft 14 which determines the stroke of the pumping fingers 18.

As shown in FIGS. 1A-1C and 2A-2B, the pumping system 100 also includes a pumping mechanism 200. The pumping mechanism 200 includes a chassis 16 that is configured for removable attachment to the disposable cassette 10 through use of a plurality of reference datum for locating and supporting the disposable cassette 10. Mounted lengthwise and parallel to the fluid path within the chassis 16 is a motor 13. In various embodiments, the motor 13 is mounted in a central portion of the chassis 16. Also mounted within the chassis 16 is a camshaft 14 that may be positioned adjacent to and in mechanical communication with the motor 13.

As used herein, the term "mechanical communication" refers to an interface or connection between two or more moveable portions such that movement of a first portion results in movement of one or more additional portions of the device. Exemplary means for moveable communication include, but are not limited to, gears 55, screw threads, and contact with a lobe of a camshaft.

Accordingly, in various embodiments, a main lobe 21 rotating on a camshaft 14 that is positioned within the chassis 16 longitudinal to the axis of flow drives a pair of parallel pumping finger drive arms 17, which pivot on separate hinges in line with the camshaft 14. The pumping finger drive arms 17 may be disposed within the chassis 14 in parallel to the motor 13, with a bottom portion of each being in mechanical communication with the camshaft 14. Thus, the pumping finger drive arms 17 are hingedly mounted to the chassis 16 and in mechanical communication with the camshaft 14. In various embodiments, the pumping finger drive arms 17 are in mechanical communication with the camshaft 14 such that they are 180 degrees out of phase with each other. As such, one chamber 30 pumps while the opposing chamber 30 fills.

Driving the pumping finger drive arms 17 with a single camshaft lobe 21 allows for the displacement and velocity profile of the fingers 17 to be optimized, which mitigates the need to vary motor speed to control the flow rate. The main lobe 21 profile is thus configured to retract the finger 17 of one chamber 30 during the fill phase of the pumping cycle and control fluid velocities by reducing restrictions to the upstream fluid path and by extending the overall duration of the filling cycle. Extreme fluid velocities increase the potential for delivery rate errors when infusing highly viscous fluids and increase the level of hemolysis from high shear damage to blood cells when infusing whole blood.

Figure 3A:
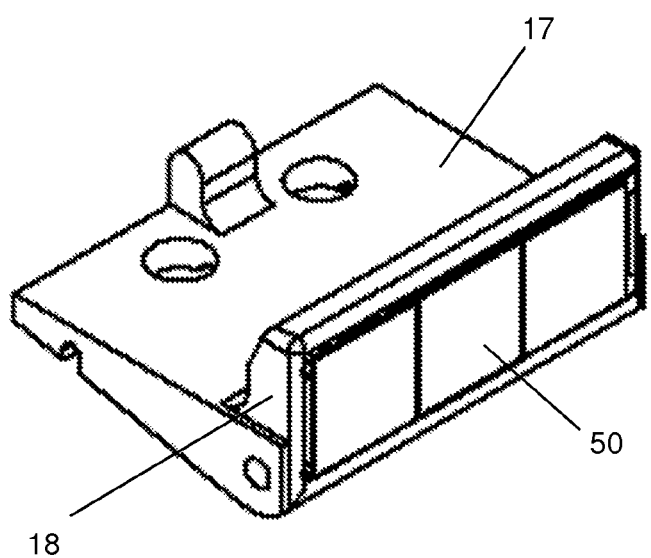
FIGS. 3A-3C are pictorial diagrams showing various views of the pumping finger magnet assembly including a strain gauge mounted thereto.
Figure 3B:
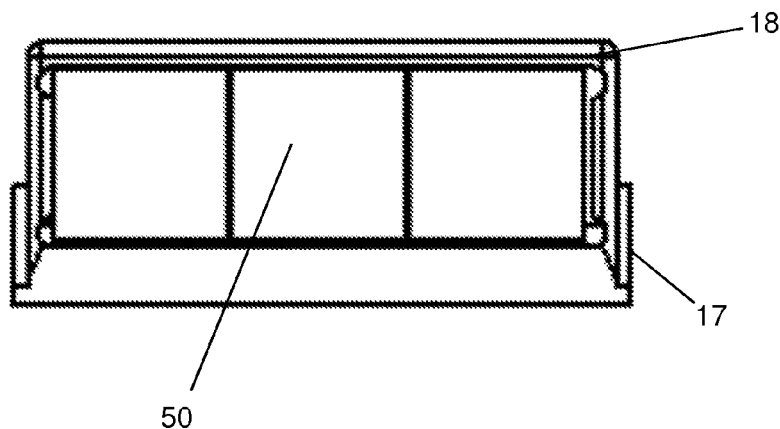
Figure 3C:
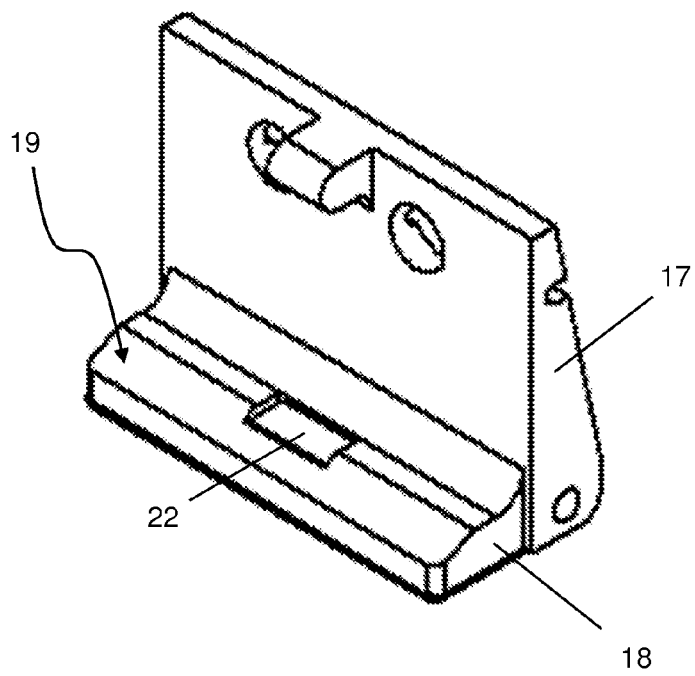
Figure 4A:
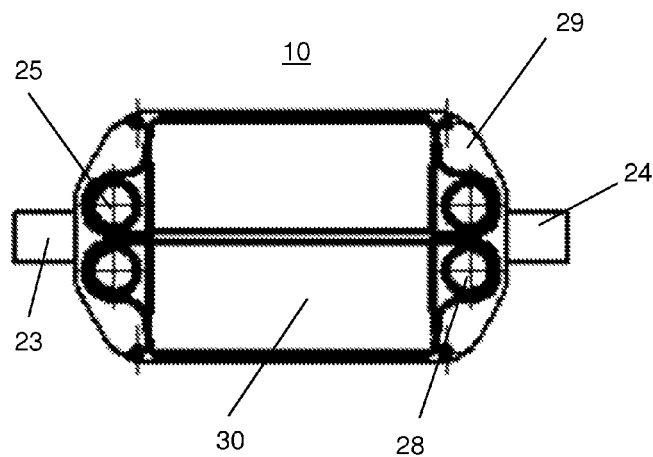
FIGS. 4A-4C are pictorial diagrams showing various views of the disposable cassette including the inlet and outlet valves of each of the pumping chambers.
Figure 4B:
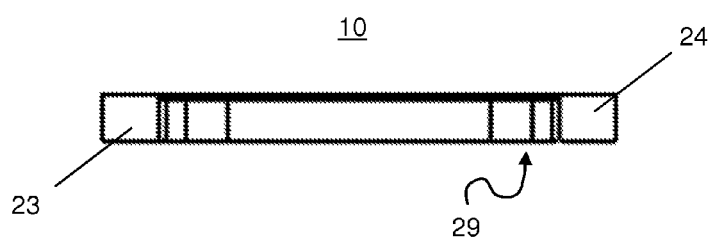
Figure 4C:
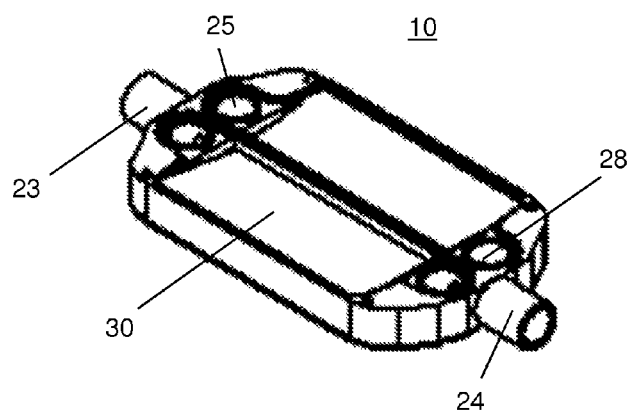

In one embodiment, provided on top portions of each of the pumping finger drive arms 17 is an array of permanent magnets 50. As shown in FIGS. 3A-3C, each magnet array 50 may be substantially rectangular in shape and configured for paramagnetic attachment to the multi-laminate membrane 32. In embodiments where electrostatic attachment to the multi-laminate membrane 32 is required, a conductive plate (not shown) may replace the magnet array 50. In yet another embodiment, the top portions of each of the pumping finger drive arms 17 may be configured for triboelectric attraction, mechanical coupling or chemical bonding to the multi-laminate membrane 32.

As shown in FIGS. 1A-1C and 2A-2B, the camshaft 14 also includes a plurality (i.e., two or four) of valve lobes 15. In various embodiments, the camshaft 14 may include two valve lobes 15, each being disposed on the camshaft 14 such that the main lobe 21 is located between the valve lobes 15. When present, the two valve lobes 15 may be referred to as the inlet valve lobe and the outlet valve lobe. Mounted to the chassis 16 on independent hinges is a plurality of valve arms 11. The lower portions of each valve arm 11 is thus in mechanical communication with one of the plurality of valve lobes 15 of the camshaft 14. The upper portions of the valve arms 11 are configured to respectively actuate the inlet 25 valves and outlet 28 valves of the disposable cassette 10. Thus, in various embodiments, the pumping mechanism 200 includes two inlet valve arms 11 that independently actuate the inlet valves 25 of the cassette 10, and two outlet valves arms 11 that independently actuate the outlet valves 28 of the cassette 10. In certain embodiments, the inlet/outlet valve arm 11 pairs are 180 degrees out of phase with each other, such that the inlet valve 25 corresponding to a first pumping chamber 30 is opened at the same time as the outlet valve 28 of a second pumping chamber 30, and vice versa. Fluid is therefore delivered sequentially from each pumping chamber 30 at a constant flow rate without the interruption of flow inherent in traditional peristaltic and cassette systems.

Pressure sensing on medical infusion instruments is required to monitor the status of the flow rate of medication. Occlusions upstream or downstream of the pump cause internal pressure in the disposable to change. Because the fluid path is sterile, pressure is typically measured through the wall of the disposable. However, the mechanical properties of conventional elastomeric membranes introduce errors in this pressure measurement because the force contribution by the elastomer cannot be isolated from the force being seen by the transducer.

Hysteresis is also a problem because elastomers have high internal friction, which cause increasing pressures to read low and decreasing pressure to read high. As used herein, the term "hysteresis" refers to the dependence of a system not only on its current environment but also on its past environment. This dependence arises because the system can be in more than one internal state.

Conventional systems use force sensors (i.e., strain gauges) that are preloaded (for load detection and to sense negative pressures) against the disposable elastomeric membrane or tube. Small surface area contact, variations in preload and effective spring rate of the elastomer, as well as hysteresis generated by internal friction in the elastomer, all contribute to the accuracy of pressure sensing system. In addition, sensor pairs are typically required to monitor both upstream and downstream pressures. However, these conventional systems are limited to sensing changes in pressure as opposed to being reliable gauge pressure measurement devices.

Referring back to FIGS. 3A-3C, the pumping system 100 may include a plurality of electronic strain gauges 22 to sense the pressure being applied by the fluid within each of the pumping chambers 30. In certain embodiments, the plurality of strain gauges 22 may be attached to the back side 19 (i.e., the side opposite to the attachment surface to the multi-laminate membrane 32) of each pump finger drive arm 17. In other embodiments, the strain gauges 22 may be disposed on an appropriate portion of the pumping finger drive arm 17 or chassis 16. In various embodiments, the pumping mechanism 200 includes one strain gauge per pumping finger.

Because the multi-laminate membrane 32 has zero spring rate and is supported against vacuum loads by electrostatic or magnetic attachment to the pumping finger drive arm 17, the multi-laminate membrane 32 does not need to be preloaded by the disposable. Additionally, because the pressure is acting over the entire top surface of the pumping finger drive arm, hysteresis is minimized and gauge pressure accuracy is far superior to other systems constrained to work through a preloaded, elastomeric interface. As such, the force measured is truly the internal pressure of the fluid within the pumping chamber 30 over the contact area of the pumping finger drive arm 17.

In addition, the strain gauges 22 can detect mechanical failures. All failures of critical-to-function components in a life sustaining medical device have to be detectable and/or mitigated. By monitoring the dynamic pressure changes generated during the course of the pumping cycle, the failure of any component in the pump mechanism can be detected. An example would be failure of one of the springs which maintains contact between the pumping finger drive arms 17 and the main lobe 21. A broken spring would cause the pressure characteristic being monitored by software to change and generate an alarm.

It should be understood that the motor 13 is electrically connected to a power source that supplies power to the motor 13 to drive the camshaft 14. Additionally, each of the motor 13, power source and/or strain gauges 22 may be electrically connected to a controller (not shown). The controller may be configured to send/receive signals to the motor 13 and/or power supply to control motor function such as speed of rotation and to turn the motor on/off. Additionally, the controller may be configured to receive signals from each of the strain gauges 22 and in response to those signals, alter motor function and/or alert a user regarding a failure.

Finally, it should be understood that the motor 13 is not working against the elastomer (most of the force generated by pump motors today is used to pinch off the disposable tubing or membrane to occlude flow). Thus, the present invention provides a significant opportunity to reduce motor size and power requirements, which has compounding benefits in reducing the overall pumping system size, frictional losses, wear and structural loads on mechanism components.

A pumping cycle of the pumping system thus proceeds as follows. The camshaft 14 spins in accordance with movement of the motor 13. During an inlet stroke of a first pumping chamber 30, the main lobe 21 of the camshaft 14 causes a first pumping finger drive arm 17 to retract from its fully extended position. Due to electrostatic or magnetic attraction between the first pumping finger drive arm 17, a vacuum is pulled within the first pumping chamber 30.

As the retraction of the first pumping finger drive arm 17 occurs, the first outlet valve 28 is closed and the first inlet valve 25 is fully opened, enabling fluid flowing from the fluid reservoir connected to the pumping system to flow through inlet port 23 and fill the first pumping chamber 30 of the cassette 10.

Moving in concert with the first pumping finger drive arm 17 is the second pumping finger drive arm 17 configured for pumping of the second pumping chamber 30. Thus, simultaneous with the filling cycle of the first pumping chamber 30, a pumping cycle occurs within the second pumping chamber 30. During an outlet stroke of the second pumping chamber 30, the main lobe 21 of the camshaft 14 causes a second pumping finger drive arm 17 to extend from its fully retracted position. Due to electrostatic or magnetic attraction between the second pumping finger drive arm 17, a positive pressure is applied to the second pumping chamber 30.

As the extending of the second pumping finger drive arm 17 occurs, the second outlet valve 28 is fully opened and the second inlet valve 25 is fully closed, enabling fluid to flow from the second pumping chamber 30 through outlet port 24 of the cassette 10 and into downstream supply tubing that may be configured for intravenous administration of the fluid to a subject.

As the first pumping finger drive arm 17 completes is retraction stroke and the second pumping finger drive arm 17 completes its extension stroke, the respective pumping finger drive arms 17 reverse direction as a result of being in mechanical communication with the camshaft 14. Thus, the first pumping finger drive arm 17 begins is extension stroke and the second pumping finger drive arm 17 begins its retraction stroke. Accordingly, fluid flow through outlet port 24 remains relatively continuous as a result of the displacement of the fluid from the first pumping chamber 30, and then from the second pumping chamber 30.

Although the invention has been described with reference to the appended Figures, it will be understood that modifications and variations are encompassed within the spirit and scope of the invention. Accordingly, the invention is limited only by the following claims.

The invention claimed is:
1. A pumping system comprising:
(a) a disposable cassette comprising:
 (i) a body having a sealed top side, an open bottom side, an inlet port disposed on a proximal end of the cassette and an outlet port disposed on a distal end of the cassette;
 (ii) a first pumping chamber disposed within the open bottom side between a first inlet valve and a first outlet valve;
 (iii) a second pumping chamber disposed within the open bottom side between a second inlet valve and a second outlet valve, wherein the first and second pumping chambers are positioned in parallel with each other; and
 (iv) a multi-laminate membrane adhered to and sealing the open bottom side defining fluid paths between the inlet port and the outlet port, wherein the multi-laminate membrane comprises a plurality of layers; and
(b) a pumping mechanism comprising:
 (i) a chassis configured for removable attachment to the disposable cassette;
 (ii) a motor disposed within a length of the chassis and positioned in parallel to an axis extending between the inlet port and the outlet port of the cassette;
 (iii) a camshaft disposed adjacent to and in mechanical communication with the motor, wherein the camshaft comprises a plurality of lobes disposed along a length thereof;
 (iv) a first drive arm hingedly attached to the chassis and positioned parallel to the motor, wherein a bottom portion of the finger drive arm is in mechanical communication with the camshaft;
 (v) a second drive arm hingedly attached to the chassis and positioned opposing the first drive arm, such that the first and second drive arms are positioned on opposing sides of the axis, wherein a bottom portion of the second drive arm is in mechanical communication with the camshaft, and wherein the first and second drive arms are 180° out of phase with each other;
 (vi) a first array of permanent magnets fixedly attached to a top portion of the first drive arm, and a second array of permanent magnets fixedly attached to a top portion of the second drive arm, wherein the first and second arrays of permanent magnets are configured for magnetic attachment to the multi-laminate membrane; and
 (v) a plurality of valve arms hingedly attached to the chassis, wherein a lower portion of each valve arm is in mechanical communication with one of the plurality of lobes on the camshaft and an upper portion of each valve arm is configured to respectively actuate each of the first and second inlet valves and the first and second outlet valves.

2. The pumping system of claim 1, wherein the camshaft comprises an inlet valve lobe and an outlet valve lobe, each disposed at opposite ends of the camshaft and 180° out of phase from each other.

3. The pumping system of claim 1, wherein the plurality of valve arms comprises a first and second inlet valve arm, and a first and second outlet valve arm, wherein the first inlet valve and second outlet valve arms are configured to actuate the respective valves simultaneously, and wherein the second inlet valve and first outlet valve arms are configured to actuate the respective valves simultaneously.

4. The pumping system of claim 1, wherein the plurality of lobes comprises a main lobe configured to actuate each of the first and second drive arms, a first valve lobe, and a second valve lobe, wherein the first valve lobe is configured to actuate the valve arms corresponding to the first and second inlet valves, and the second valve lobe is configured to actuate the valve arms corresponding to the first and second outlet valves.

5. The pumping system of claim 1, wherein an inner surface of the first pumping chamber and an inner surface of the second pumping chamber are angled in accordance with a range of motion of each of the first and second drive arms.

6. The pumping system of claim 1, wherein the multi-laminate membrane is a thin film magnetic membrane or a conductive membrane.

7. The pumping system of claim 6, wherein the thin film multi-laminate membrane comprises a first layer configured to adhere to the open bottom side of the body, a second layer configured to be magnetic and electrically conductive, and a third layer configured to resist abrasion, wherein the first, second, and third layers are laminated as a single membrane.

8. The pumping system of claim 1, further comprising a plurality of strain gauges disposed on the pumping mechanism and configured to monitor fluid pressure within the first and second pumping chambers.

9. The pumping system of claim 8, wherein the plurality of strain gauges comprises a first and a second strain gauge, each disposed on one of the first and second drive arms.

10. The pumping system of claim 8, wherein the plurality of strain gauges comprises a first and a second strain gauge, each disposed on a surface of one of the first and second drive arms in contact with the multi-laminate membrane.

11. The pumping system of claim 9, wherein the first and second strain gauges are disposed on a surface opposite to the magnetic attachment to the multi-laminate membrane.

12. The pumping system of claim 1, wherein the inlet port is configured for fluid communication with a fluid reservoir and the outlet port is configured for attachment to downstream supply tubing for intravenous administration of the fluid to a subject.

13. The pumping system of claim 1, wherein the first array of permanent magnets are arranged to span from a proximal end of the first pumping chamber to the distal end of the first pumping chamber; and the second array of permanent magnets are arranged to span from the proximal end of the first pumping chamber to the distal end of the first pumping chamber.

14. The pumping system of claim 1, wherein the first array of permanent magnets are arranged parallel to the direction of the axis; and the second array of permanent magnets are arranged parallel to the direction of the axis.

15. The pumping system of claim 1, wherein the multi-laminate membrane comprises a first layer, a second layer and a third layer, in this order, and the second layer comprises a material that is configured to magnetically attach to the first and second arrays of permanent magnets.

16. A pumping mechanism comprising:
(a) a chassis configured for removable attachment to a disposable cassette having an inlet port on a proximal end and an outlet port on a distal end;
(b) a motor disposed within a length of the chassis and positioned in parallel to an axis extending from the inlet port to the outlet port of the cassette;
(c) a camshaft disposed adjacent to and in mechanical communication with the motor, the camshaft positioned in parallel to the axis, wherein the camshaft comprises a plurality of lobes disposed along a length thereof;
(d) a first drive arm hingedly attached to the chassis and positioned parallel to the motor, wherein a bottom portion of the first drive arm is in mechanical communication with the camshaft;
(e) a second drive arm hingedly attached to the chassis and positioned opposing the first drive arm, wherein a bottom portion of the second drive arm is in mechanical communication with the camshaft, and wherein the first and second drive arms are 180° out of phase with each other;
(f) a first array of permanent magnets fixedly attached to a top portion of the first drive arm, and a second array of permanent magnets fixedly attached to a top portion of the second drive arm, wherein the permanent magnets are configured for magnetic attachment to a multi-laminate membrane of the disposable cassette when attached thereto;
(g) a plurality of strain gauges disposed on a surface of each of the first and second drive arms in contact with the multi-laminate membrane and configured to monitor fluid pressure within first and second pumping chambers of the disposable cassette when attached thereto; and
(h) a plurality of valve arms hingedly attached to the chassis, wherein a lower portion of each valve arm is in mechanical communication with one of the plurality of lobes on the camshaft and an upper portion of each valve arm is configured to respectively actuate each of a first inlet valve and a second inlet valve of the cassette and a first outlet valve and a second outlet valve of the cassette.

17. The pumping mechanism of claim 16, wherein the plurality of strain gauges comprises a first and a second strain gauge, each disposed on the surface of a respective drive arm.

18. The pumping mechanism of claim 16, wherein the plurality of strain gauges comprises a first and a second strain gauge, and the first and second strain gauges are disposed on the surface opposite to the attachment to the multi-laminate membrane of the disposable cassette when attached thereto.

19. The pumping mechanism of claim 16, wherein the first and second drive arms are positioned on opposing sides of the axis.

20. The pumping mechanism of claim 19, wherein the first array of permanent magnets are arranged parallel to the direction of the axis; and the second array of permanent magnets are arranged parallel to the direction of the axis.

21. The pumping mechanism of claim 16, wherein the first drive arm is symmetrical to the second drive arm along the axis.

* * * * *